(12) United States Patent
Endo et al.

(10) Patent No.: US 12,064,574 B2
(45) Date of Patent: Aug. 20, 2024

(54) PUNCTURE NEEDLE AND METHOD OF USING GUIDE WIRE

(71) Applicant: OLYMPUS CORPORATION, Tokyo (JP)

(72) Inventors: Takuo Endo, Tokyo (JP); Tomofumi Katayama, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 844 days.

(21) Appl. No.: 17/148,799

(22) Filed: Jan. 14, 2021

(65) Prior Publication Data

US 2021/0162181 A1 Jun. 3, 2021

Related U.S. Application Data

(63) Continuation of application No. PCT/JP2018/027058, filed on Jul. 19, 2018.

(51) Int. Cl.
*A61M 25/06* (2006.01)
*A61B 1/018* (2006.01)
(Continued)

(52) U.S. Cl.
CPC ............. *A61M 25/06* (2013.01); *A61B 1/018* (2013.01); *A61B 8/12* (2013.01); *A61B 17/3403* (2013.01);
(Continued)

(58) Field of Classification Search
CPC ................. A61M 25/06; A61M 25/09; A61M 2025/0681; A61B 8/12; A61B 17/3496; A61B 17/3478; A61F 2/966
See application file for complete search history.

(56) References Cited

U.S. PATENT DOCUMENTS

| 5,009,642 A * | 4/1991 | Sahi ................. A61M 25/0643 |
| | | 604/110 |
| 2006/0009737 A1 | 1/2006 | Whiting et al. |

(Continued)

FOREIGN PATENT DOCUMENTS

| JP | 2004-275594 A | 10/2004 |
| JP | 2005-329078 A | 12/2005 |

(Continued)

OTHER PUBLICATIONS

International Search Report dated Sep. 4, 2018 received in International Application No. PCT/JP2018/027058, together with an English-language translation.

(Continued)

*Primary Examiner* — Leslie R Deak
(74) *Attorney, Agent, or Firm* — Scully, Scott, Murphy & Presser, P.C.

(57) ABSTRACT

The present invention relates a puncture needle includes: a sheath having a longitudinal axis; a needle tube that is arranged inside the sheath to be moved along the longitudinal axis and that has a needle tip; and a protective tube that is arranged inside the needle tube to be moved along the longitudinal axis and that has a lumen into which a guide wire is inserted. The needle tube has a step portion formed at a position midway along the needle tube. The protective tube has a protrusion, which protrudes radially outward, on an outer peripheral surface thereof at a position midway nearer a proximal end side of the protective tube than the step portion is. A distal end of the protective tube is positioned at a position to protrude from the distal end of the needle tube when the protrusion abuts the step portion.

20 Claims, 15 Drawing Sheets

(51) Int. Cl.
*A61B 8/12* (2006.01)
*A61B 17/34* (2006.01)
*A61F 2/966* (2013.01)
*A61M 25/09* (2006.01)
*A61M 27/00* (2006.01)

(52) U.S. Cl.
CPC .............. *A61F 2/966* (2013.01); *A61M 25/09* (2013.01); *A61M 27/002* (2013.01); *A61B 2017/3413* (2013.01); *A61M 2025/0681* (2013.01)

(56) References Cited

U.S. PATENT DOCUMENTS

| | | |
|---|---|---|
| 2010/0036316 A1 | 2/2010 | Agrawal |
| 2010/0312141 A1 | 12/2010 | Keast et al. |
| 2013/0331734 A1 | 12/2013 | Keast et al. |
| 2014/0194776 A1 | 7/2014 | Gunday et al. |
| 2014/0371676 A1 | 12/2014 | Leeflang et al. |
| 2016/0045715 A1* | 2/2016 | Galgano ........... A61M 25/0662 604/510 |
| 2016/0157839 A1* | 6/2016 | Eckerline .............. A61M 25/09 600/567 |
| 2017/0007217 A1 | 1/2017 | Keast et al. |
| 2018/0085142 A1 | 3/2018 | Leeflang et al. |
| 2018/0153532 A1 | 6/2018 | Keast et al. |
| 2019/0069886 A1 | 3/2019 | Eckerline et al. |
| 2020/0069154 A1 | 3/2020 | Endo et al. |
| 2021/0008347 A1 | 1/2021 | Galgano et al. |
| 2021/0290262 A1 | 9/2021 | Leeflang et al. |

FOREIGN PATENT DOCUMENTS

| | | |
|---|---|---|
| JP | 2008-194112 A | 8/2008 |
| JP | 2016-502891 A | 2/2016 |
| WO | 2006/017061 A2 | 2/2006 |
| WO | 2008/118330 A2 | 10/2008 |
| WO | 2014/109871 A1 | 7/2014 |
| WO | 2014/165783 A1 | 10/2014 |
| WO | 2014/182969 A1 | 11/2014 |
| WO | 2016/002835 A1 | 1/2016 |
| WO | 2016/089558 A1 | 6/2016 |
| WO | 2018/220850 A1 | 12/2018 |

OTHER PUBLICATIONS

Extended European Search Report dated Mar. 28, 2022 received in 18926687.7.

* cited by examiner

PUNCTURE NEEDLE AND METHOD OF USING GUIDE WIRE

CROSS-REFERENCE TO RELATED APPLICATIONS

This is a continuation of International Application PCT/JP2018/027058, with an international filing date of Jul. 19, 2018, which is hereby incorporated by reference herein in its entirety.

TECHNICAL FIELD

The present invention relates to a puncture needle and a method of using a guide wire.

BACKGROUND ART

There is a known technique in which a guide wire is introduced into the inside of a body via an inner hole of a needle tube that has punctured the tissue of the body (for example, refer to US Patent Application Publication No. 2016/0157839).

In US Patent Application Publication No. 2016/0157839, in order to prevent the guide wire from being damaged by the edge of the distal end of the needle tube, an inner cylinder, which protrudes from the distal end of the needle tube, is inserted into the inner hole of the needle tube and the guide wire is made to protrude through an inner hole of the inner cylinder.

SUMMARY OF INVENTION

An aspect of the present invention provides a puncture needle that includes: a tubular sheath having a longitudinal axis; a needle tube that is arranged inside the sheath so as to be movable along the longitudinal axis and that has a needle tip at a distal end thereof; a protective tube that is arranged inside the needle tube so as to be movable along the longitudinal axis and that has a lumen into which a guide wire is inserted so as to be movable along a direction of the longitudinal axis; a needle slider that is connected to a proximal end of the needle tube; and a tube slider that is supported so as to be able to move in directions along the longitudinal axis relative to the needle slider and that is connected to the proximal end of the protective tube. The needle tube has a step portion formed at a position midway along the needle tube in the longitudinal direction. The protective tube has a protrusion, which protrudes radially outward, on at least part of an outer peripheral surface thereof at a position which is nearer a proximal end side of the protective tube than the step portion is. A distal end of the protective tube is positioned at a position so as to protrude from the distal end of the needle tube when the protrusion abuts the step portion from the proximal end side of the protective tube. The needle slider is provided with a locking portion that abuts the tube slider when the tube slider is moved forward toward the distal end side relative to the needle slider, and the protrusion is maintained in a state of pressing against the step portion when the tube slider is moved forward to a position where the tube slider abuts the locking portion.

DESCRIPTION OF EMBODIMENTS

Figure 1:
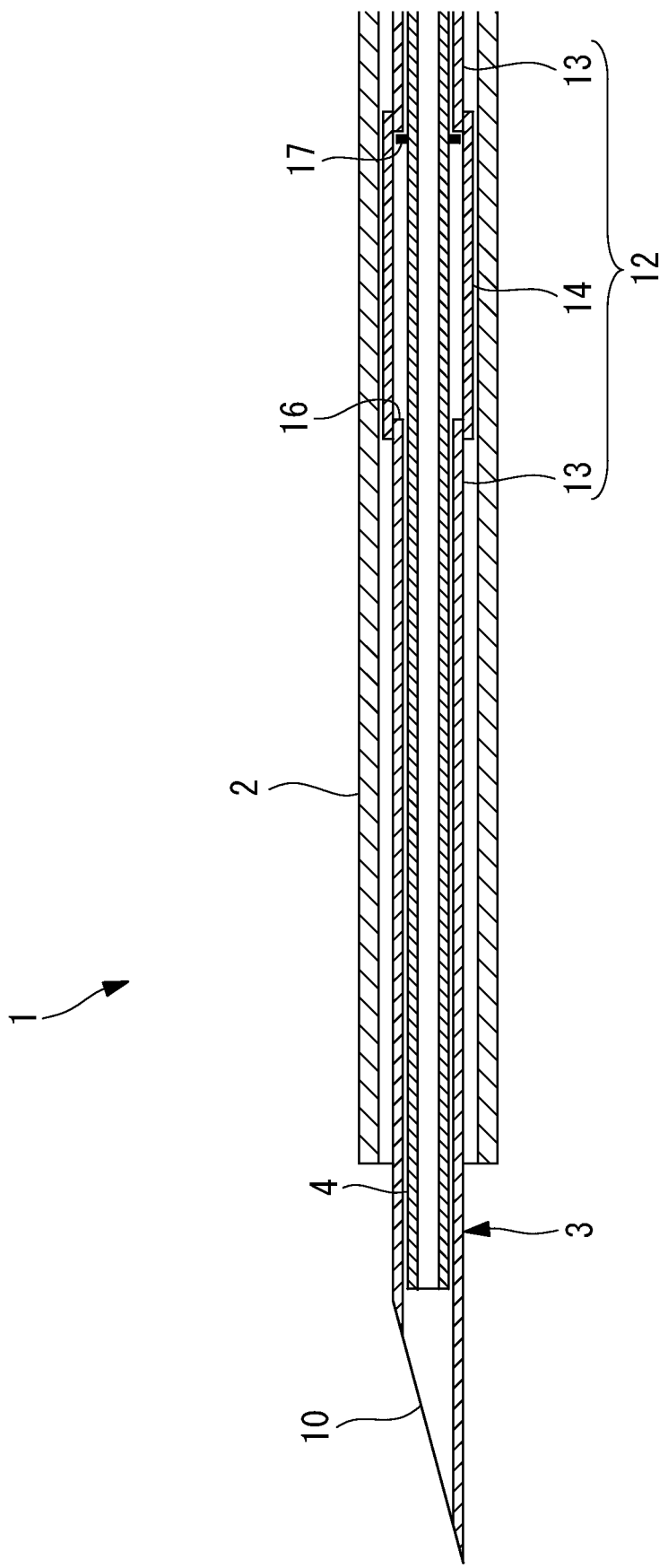
FIG. 1 is a partial longitudinal sectional view illustrating a tip portion of a puncture needle according to an embodiment of the present invention.

Hereafter, a puncture needle 1 and a method of using a guide wire 15 according to an embodiment of the present invention will be described while referring to the drawings.

As illustrated in FIG. 1, the puncture needle 1 according to this embodiment includes a tubular sheath 2 having a longitudinal axis, a needle tube 3 that is arranged inside the sheath so as to be movable along the longitudinal axis, and a protective tube 4 that is arranged so as to be movable inside the needle tube 3 in the longitudinal axis directions.

Figure 2:
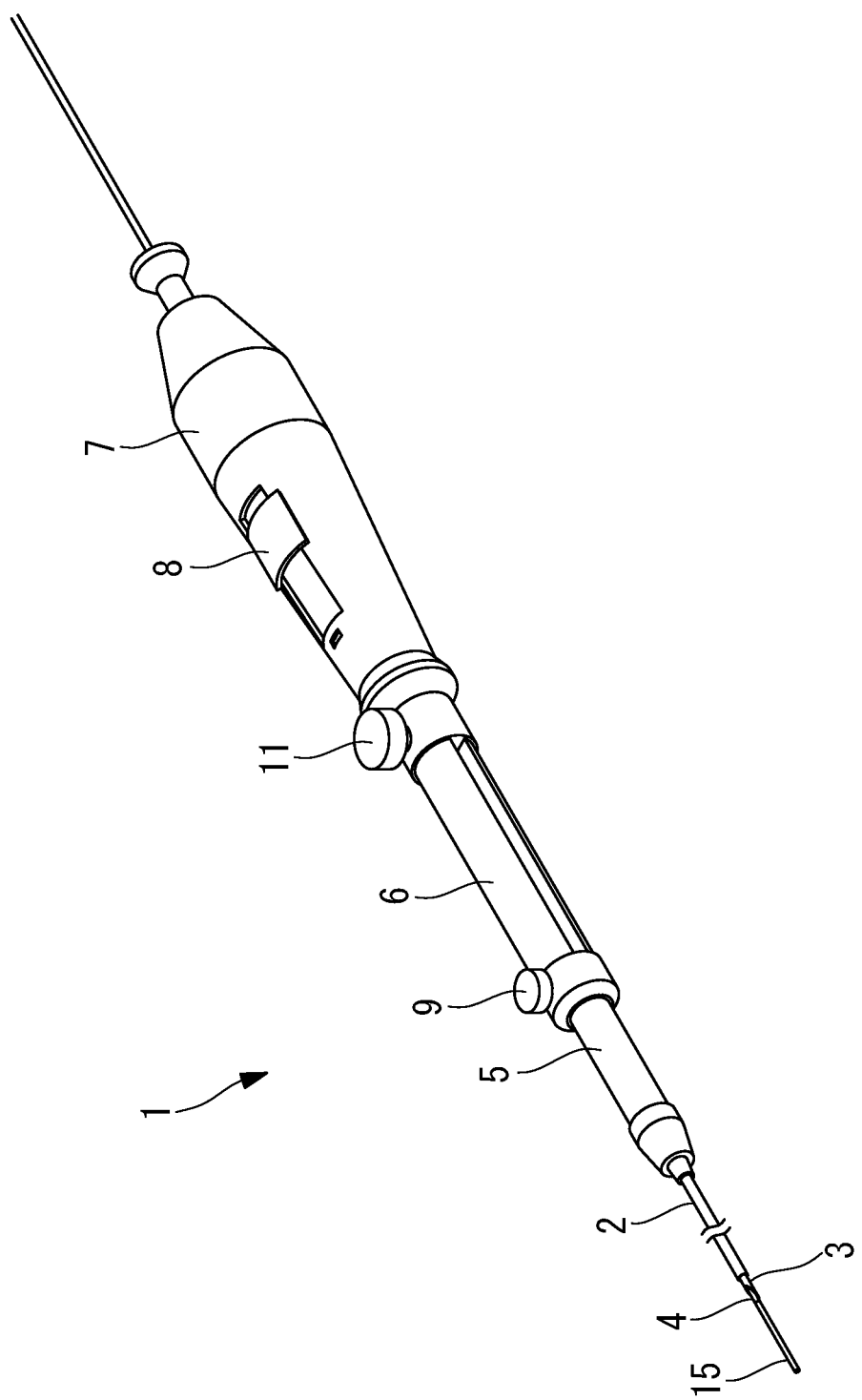
FIG. 2 is a perspective view illustrating the entire puncture needle in FIG. 1.
Figure 3:
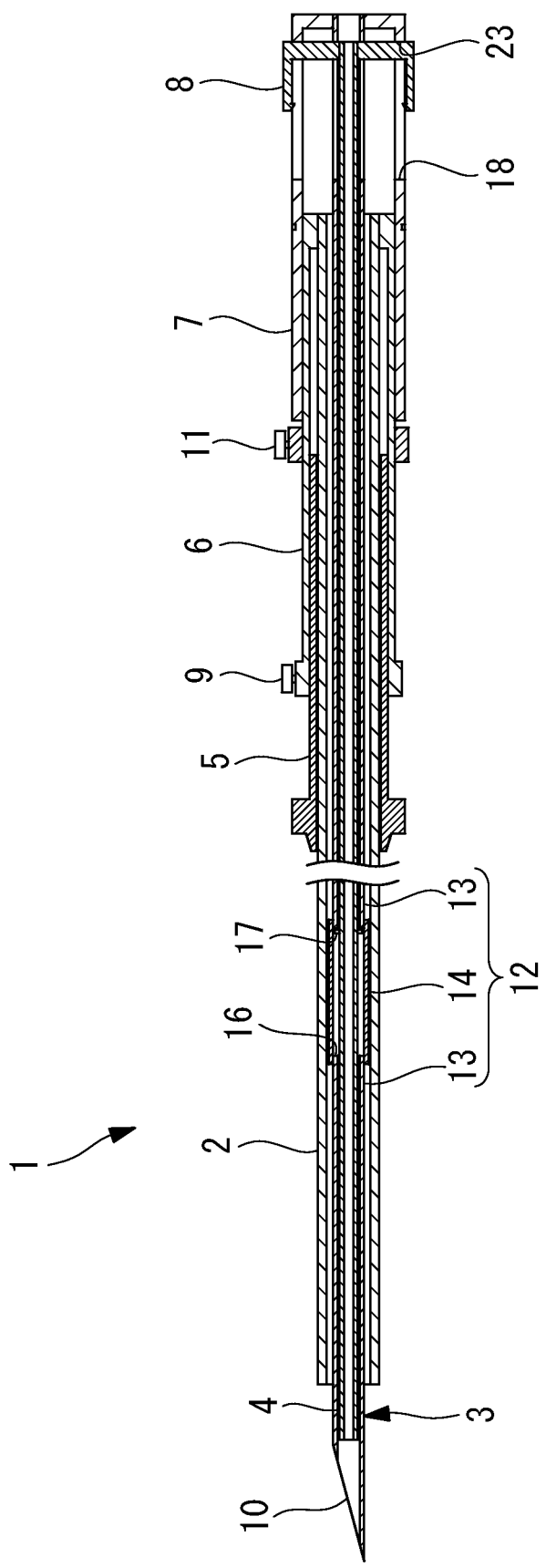
FIG. 3 is a longitudinal sectional view illustrating the entire puncture needle in FIG. 2.

As illustrated in FIGS. 2 and 3, the puncture needle 1 includes an operation part body 5 that is grasped by an operator, a sheath slider 6 to which a proximal end of the sheath 2 is fixed and that is supported so as to be movable in the longitudinal axis directions with respect to the operation part body 5, a needle slider 7 that is supported so as to be movable in directions along the longitudinal axis with respect to the sheath slider 6, and a tube slider 8 that is supported so as to be movable in the longitudinal axis directions with respect to the needle slider 7. The sheath slider 6 is provided with a fixing screw 9 for fixing the sheath slider 6 to the operation part body 5 at an arbitrary position.

Figure 4:
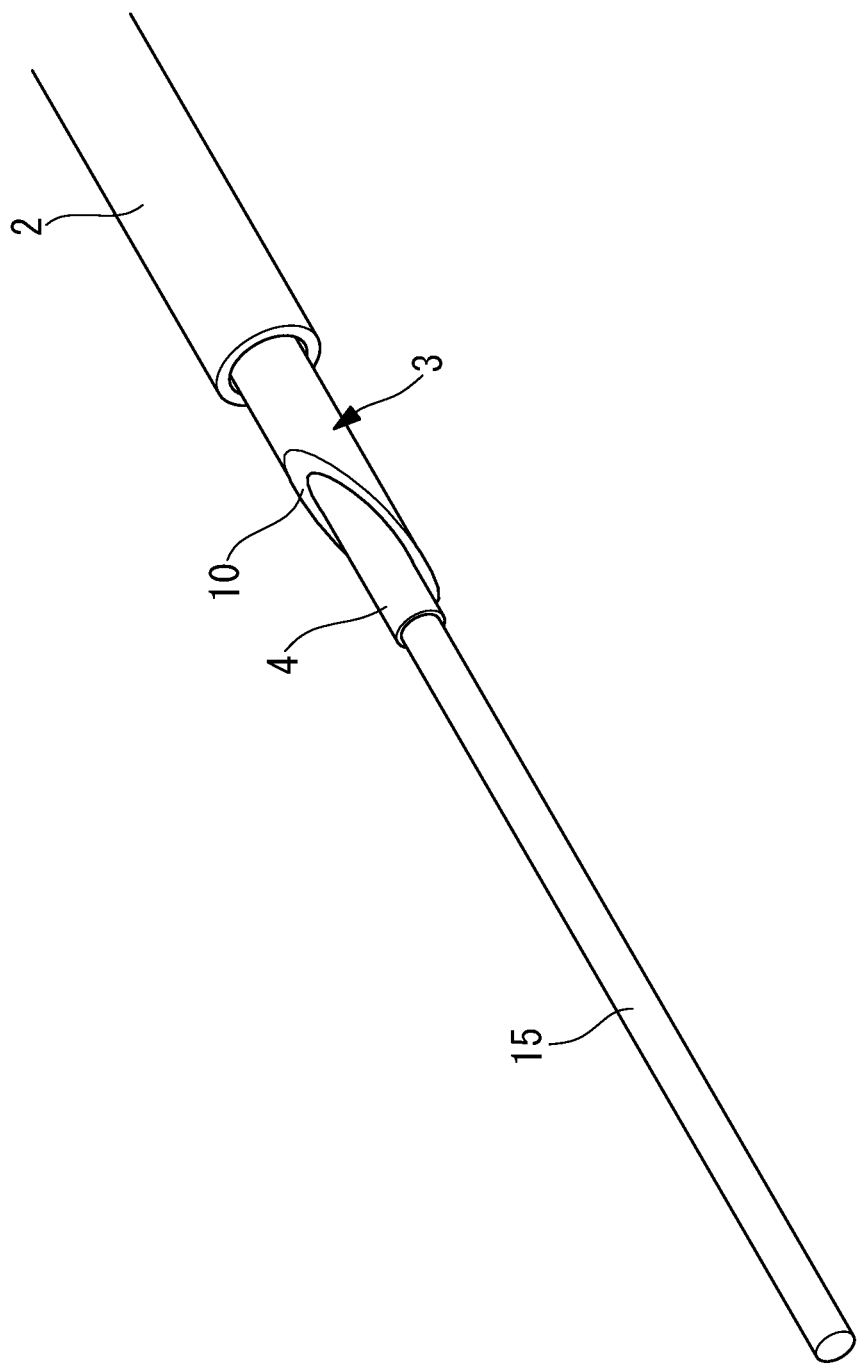
FIG. 4 is a perspective view illustrating the tip portion of the puncture needle in FIG. 1.

As illustrated in FIG. 4, the sheath 2 is formed in a tubular shape having a circular cross section. The proximal end of the sheath 2 is fixed to the sheath slider 6.

As illustrated in FIG. 4, the needle tube 3 has a circular cross section, which has an outer diameter that is slightly smaller than the inner diameter of the sheath 2, and the needle tube 3 has a needle tip 10 having a shape resulting from the distal end of the needle tube 3 being diagonally cut at a plane intersecting the longitudinal axis. The proximal end of the needle tube 3 is fixed to the needle slider 7. The needle tube 3 can be moved forward and backward in the longitudinal axis directions relative to the sheath 2 by moving the needle slider 7 along the longitudinal axis directions relative to the sheath slider 6. The sheath slider 6 is provided with a needle stopper 11 that adjustably defines a forward position of the needle slider 7 with respect to the sheath slider 6.

As illustrated in FIG. 4, the protective tube 4 also has a circular cross section that is slightly smaller than the inner diameter of the needle tube 3. The inner diameter of the protective tube 4 is larger than the outer diameter of the guide wire 15. In other words, the guide wire 15 can be inserted into the inside of a lumen of the protective tube 4 so as to be movable in the longitudinal axis directions. The proximal end of the protective tube 4 is fixed to the tube slider 8. The protective tube 4 can be moved forward and backward in the longitudinal axis directions relative to the needle tube 3 by moving the tube slider 8 along the longitudinal axis directions relative to the needle slider 7.

The protective tube 4 is composed of a resin material having a comparatively high rigidity such as polyether ether ketone resin (PEEK). Polypropylene or PET, as resin materials having a comparatively high rigidity, may be used instead of PEEK.

The protective tube 4 may be formed of a material that can be detected by an ultrasound sensor. In addition, the tip portion of the protective tube 4 may be coated with a metal powder. This enables the protruding state of the protective tube 4 to be readily visible under x-ray or ultrasound endoscopy.

In this embodiment, as illustrated in FIG. 1, the needle tube 3 has a joint section 12 at a position midway therealong in the longitudinal axis direction and two tubular parts 13 that each include either the needle tip 10 or the proximal end of the needle tube 3. The joint section 12 is formed by arranging the end surfaces of the two tubular parts (needle tip portion and needle base portion) 13, which constitute the needle tube 3, in the longitudinal axial direction with a space therebetween and joining the end surfaces to each other in a state where the two tubular parts 13 have been fitted into the inside of a large-diameter connection tube 14. Thus, inside the joint section 12, a step portion 16 is formed by the connection tube 14 and a proximal end surface of the tubular part 13 arranged at the side nearer the distal end, the inner diameter decreasing by one step in the step portion 16 in the direction toward the distal end.

A protrusion 17 that protrudes radially outward is provided on the outer surface of the protective tube 4 at a position that is midway therealong in the longitudinal axis direction and coincides with the connection tube 14. The outer diameter of the protrusion 17 is set to be larger than the inner diameter of the tubular parts 13 of the needle tube 3 and smaller than the inner diameter of the connection tube 14 of the needle tube 3.

Figure 5:
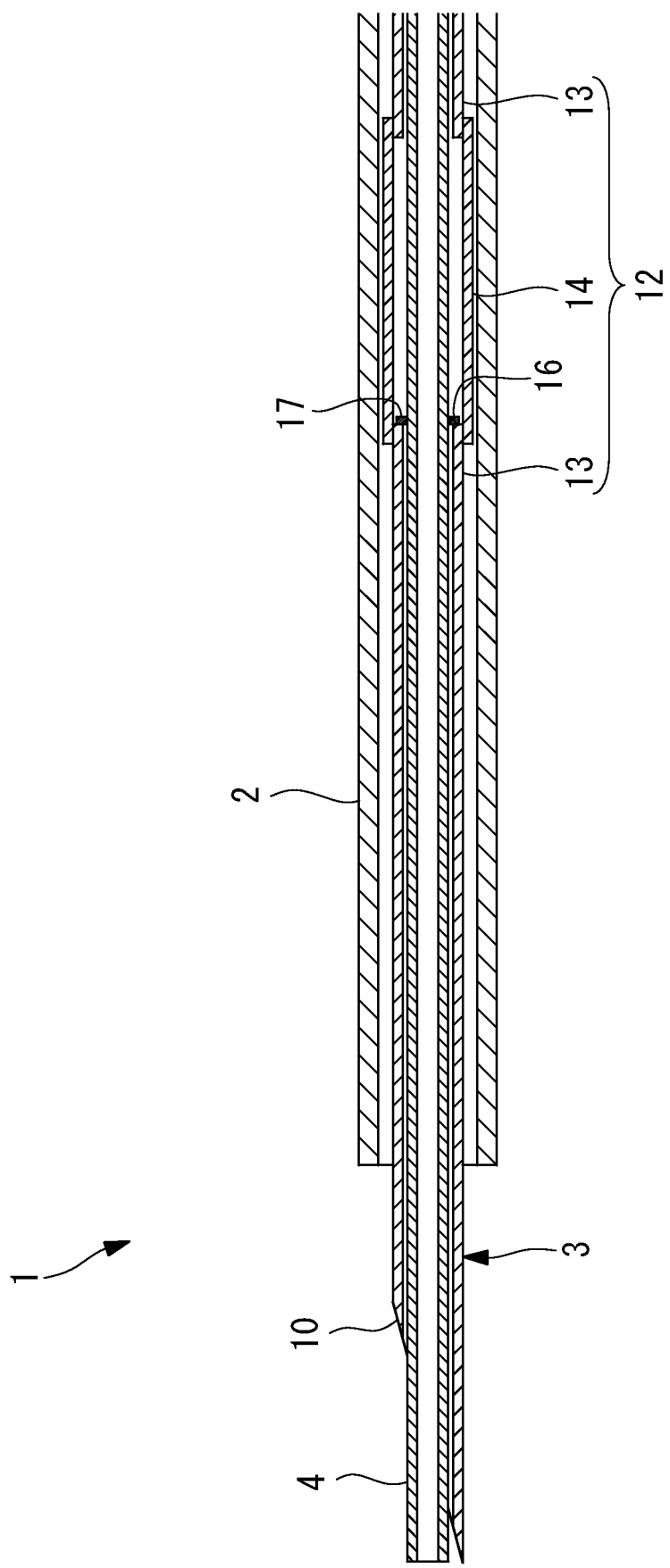
FIG. 5 is a partial longitudinal sectional view illustrating a state in which a protective tube is made to protrude from a needle tip of the puncture needle in FIG. 1.

Thus, the amount of movement of the protective tube 4 in the longitudinal axis direction with respect to the needle tube 3 is restricted to a distance between a position where the protrusion 17 abuts the proximal end surface of the distal end-side tubular part 13 and a position where the protrusion 17 abuts the distal end surface of the proximal-end-side tubular part 13. As illustrated in FIG. 5, the distal end of the protective tube 4 is positioned at a position where the distal end of the protective tube 4 protrudes from the distal end of the needle tube 3 by a prescribed dimension at the position where the protrusion 17 abuts the step portion 16 formed by the proximal end surface of the distal end-side tubular part 13.

Figure 6:
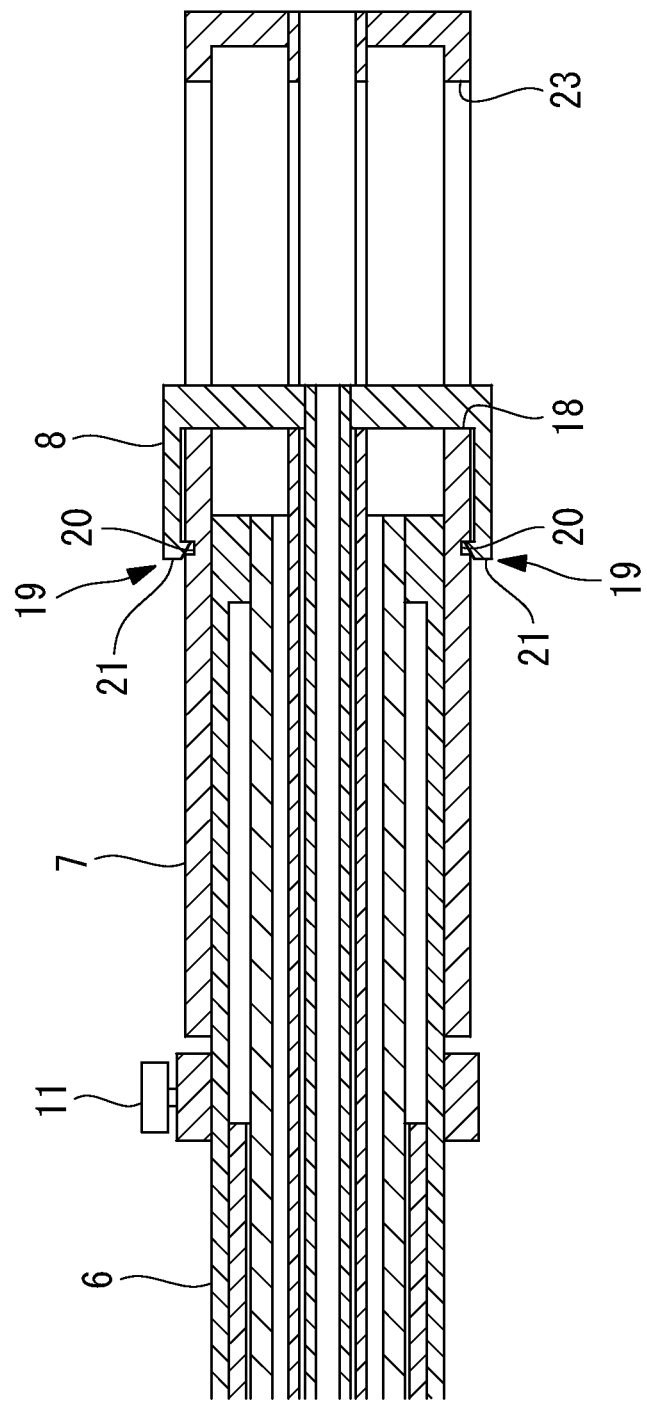
FIG. 6 is a longitudinal sectional view illustrating the relationship between a tube slider and a needle slider of the puncture needle in FIG. 1.

As illustrated in FIG. 6, the needle slider 7 is provided with a stopper (locking portion) 18 that abuts the tube slider 8 when the tube slider 8 is moved forward in the longitudinal axis direction to the maximum extent. A fixing mechanism 19 that fixes the tube slider 8 to the needle slider 7 in a state where the tube slider 8 has abutted the stopper 18 is provided between the needle slider 7 and the tube slider 8.

The fixing mechanism 19, for example, includes a recess 20 that is provided in the needle slider 7 and a hook 21 that is provided on the tube slider 8, and backward movement of the tube slider 8 relative to the needle slider 7 is restricted as a result of the hook 21 catching in the recess 20 when the tube slider 8 is moved forward.

Here, the maximum stroke of the tube slider 8 with respect to the needle slider 7 is set to be greater than the amount of protrusion of the protective tube 4 from the needle tip 10 when the tube slider 8 is moved forward to a position where the protrusion 17 of the protective tube 4 abuts the step portion 16 of the needle tube 3.

In other words, when the tube slider 8 is moved forward relative to the needle slider 7, the protrusion 17 of the protective tube 4 abuts the step portion 16 of the needle tube 3 in the middle of the stroke and any further protrusion of the protective tube 4 beyond the needle tip 10 is restricted. At this point, further forward movement of the tube slider 8 relative to the needle slider 7 is possible, and the protective tube 4 is made to elastically deform by an amount equivalent to the gap inside the needle tube 3 by moving the tube slider 8 forward relative to the needle slider 7. When the tube slider 8 is moved forward relative to the needle slider 7 by the maximum stroke, the tube slider 8 abuts the stopper 18 and further forward movement of the tube slider 8 is restricted, and the hook 21 catches in the recess 20 of the fixing mechanism 19 and backward movement of the tube slider 8 relative to the needle slider 7 is restricted.

Thus, the protective tube 4 is arranged so as to protrude from the needle tip 10 of the needle tube 3 by a prescribed dimension and the protrusion 17 of the protective tube 4 is maintained in a state in which the protrusion 17 is pressed against the step portion 16 of the needle tube 3 by the elastic deformation of the protective tube 4. As a result, the protective tube 4 is maintained in a state of protruding from the needle tip 10 of the needle tube 3 by a predetermined dimension, even if there is a difference between the path lengths of the needle tube 3 and the protective tube 4 due to the needle tube 3 being bent.

Hereafter, a method of using the guide wire 15 in which the puncture needle 1 according to this embodiment is used will be described.

In order to position the guide wire 15 inside a body using the puncture needle 1 according to this embodiment, first, the needle slider 7 is moved backward relative to the sheath slider 6 to the most rearward point, and the tube slider 8 is moved backward relative to the needle slider 7 to the most rearward point (second position). As a result, the needle tip 10 of the needle tube 3 is arranged so as to be retracted into the inside of the sheath 2, and the protective tube 4 is arranged so as to be retracted toward the proximal end side from the needle tip 10 of the needle tube 3 and preparation of the puncture needle 1 is thus completed.

The sheath 2 of the thus-prepared puncture needle 1 is inserted from an opening at the proximal end of a channel 110 of an ultrasound endoscope (endoscope) 100, which includes an ultrasound sensor that is not illustrated, up to the vicinity of the position of the distal end of the channel 110. In this state, the ultrasound endoscope 100 is inserted into the inside of the stomach (first lumen) while acquiring tomographic images of the inside of the body by operating the ultrasound sensor and checking the acquired tomographic images. The opening at the distal end of the channel 110 in the ultrasound endoscope 100 is then arranged opposite the part of the stomach wall that is to be punctured.

In this state, the sheath slider 6 is moved forward relative to the operation part body 5 so that the distal end of the sheath 2 protrudes from the opening at the distal end of the channel 110. Then, the needle slider 7 is moved forward relative to the sheath slider 6 with the distal end of the sheath 2 positioned opposite the part of the stomach wall that is to be punctured. As a result, the needle tip 10 of the needle tube 3 protrudes from the inside of the sheath 2, the part of the stomach wall opposite the distal end of the sheath 2 is punctured by the needle tube 3, and a through hole is formed by the needle tube 3 puncturing the stomach and the bile duct (second lumen) adjacent to the outside of the stomach.

Then, the tube slider 8 is moved forward relative to the needle slider 7 with the needle tube 3 protruding to a position where the needle tube 3 will pass through the through hole.

When the tube slider 8 is moved forward, the protective tube 4 is moved forward relative to the needle tube 3, and as illustrated in FIG. 5, the protective tube 4 is moved to a position where the distal end of the protective tube 4 protrudes from the needle tip 10 of the needle tube 3 (first position).

Then, further protrusion of the protective tube 4 is restricted by the protrusion 17 provided on the protective tube 4 abutting, from the proximal end side, the step portion 16 provided on the inner surface of the needle tube 3. In this case, in this embodiment, even in the state where movement of the distal end of the protective tube 4 is restricted, the tube slider 8 can be moved further forward relative to the needle slider 7, and as illustrated in FIG. 6, the tube slider 8 is fixed by the fixing mechanism 19 at a position where the tube slider 8 abuts the stopper 18.

In other words, the protective tube 4 is elastically deformed by an amount equivalent to a gap inside the needle tube 3, and as a result, the protective tube 4 is maintained in a state where the distal end is constantly urged forward and the protrusion 17 of the protective tube 4 is pressed against the step portion 16 inside the needle tube 3 from the proximal end side. Therefore, the protective tube 4 is maintained in a state of protruding from the needle tip 10 by an appropriate amount even when there is a difference between the path lengths of the needle tube 3 and the protective tube 4 as a result of the needle tube 3 being bent due to the insertion path thereof inside the body cavity.

In this state, the guide wire 15 is inserted into the lumen of the protective tube 4 from the proximal end side of the protective tube 4, as illustrated in FIG. 1, and the guide wire 15 can be prevented from coming into contact with the needle tip 10 by making the guide wire 15 protrude from the distal end of the protective tube 4, as illustrated in FIG. 4. In other words, since the protective tube 4 is arranged so as to line the inner surface of the needle tip 10, there is an advantage that it is possible to reliably prevent the occurrence of a problem in which the guide wire 15, which is made to protrude or be retracted from the distal end of the protective tube 4, contacts and rubs against the needle tip 10.

After that, the guide wire 15 can be positioned with the guide wire 15 extending from the stomach to the bile duct by removing the needle tube 3 and the protective tube 4 from the through hole.

A tip portion of a stent deploying device, which is not illustrated, is inserted into the bile duct along a guide wire X that has been positioned in the bile duct from the stomach. The wall of the stomach and the wall of the bile duct can be connected to each other by a stent by deploying a stent from the stent deploying device, the distal end of which has been inserted into the bile duct, and then dilating the distal end of the deployed stent in the bile duct and dilating the proximal end of the stent in the stomach.

Prior to deploying the stent to the position of the wall of the bile duct, a device for dilating the hole in the wall, such as a balloon dilator, may be inserted along the guide wire 15 up to the vicinity of the wall of the bile duct in order to dilate the hole in the wall of the bile duct in advance before positioning the stent. Dilation of a hole in a wall is not limited to being performed only on the wall of the bile duct, and may instead be performed only on the wall of the stomach or on both the wall of the bile duct and the wall of the stomach.

In order to maintain the protective tube 4 in a state of protruding from the needle tip 10 regardless of how the needle tube 3 and the protective tube 4 are bent by simply maintaining the protrusion 17 of the protective tube 4 in a state of abutting the step portion 16 provided on the needle tube 3, the step 16 and the protrusion 17 are preferably arranged as far as possible toward the distal end of the puncture needle 1. However, provided that the protective tube 4 can be maintained in a state of protruding from the needle tip 10 for realistically anticipated curvatures, the step portion 16 and protrusion 17 may be arranged at the proximal end side.

Figure 7:
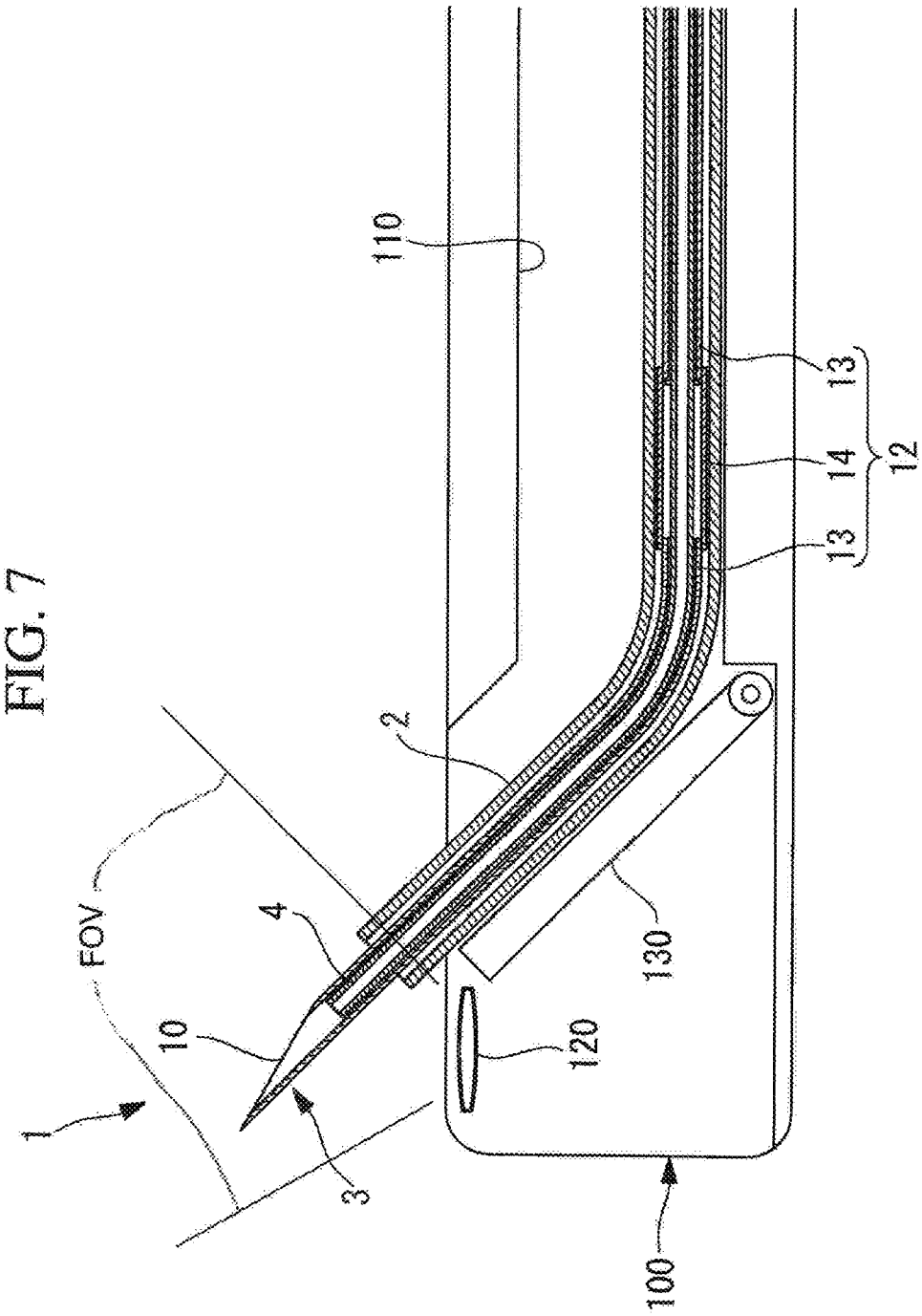
FIG. 7 is a longitudinal sectional view illustrating an example of the positional relationship between a raising platform of an endoscope that has the puncture needle in FIG. 1 inserted into a channel thereof and a joint section provided in the puncture needle.
Figure 8:
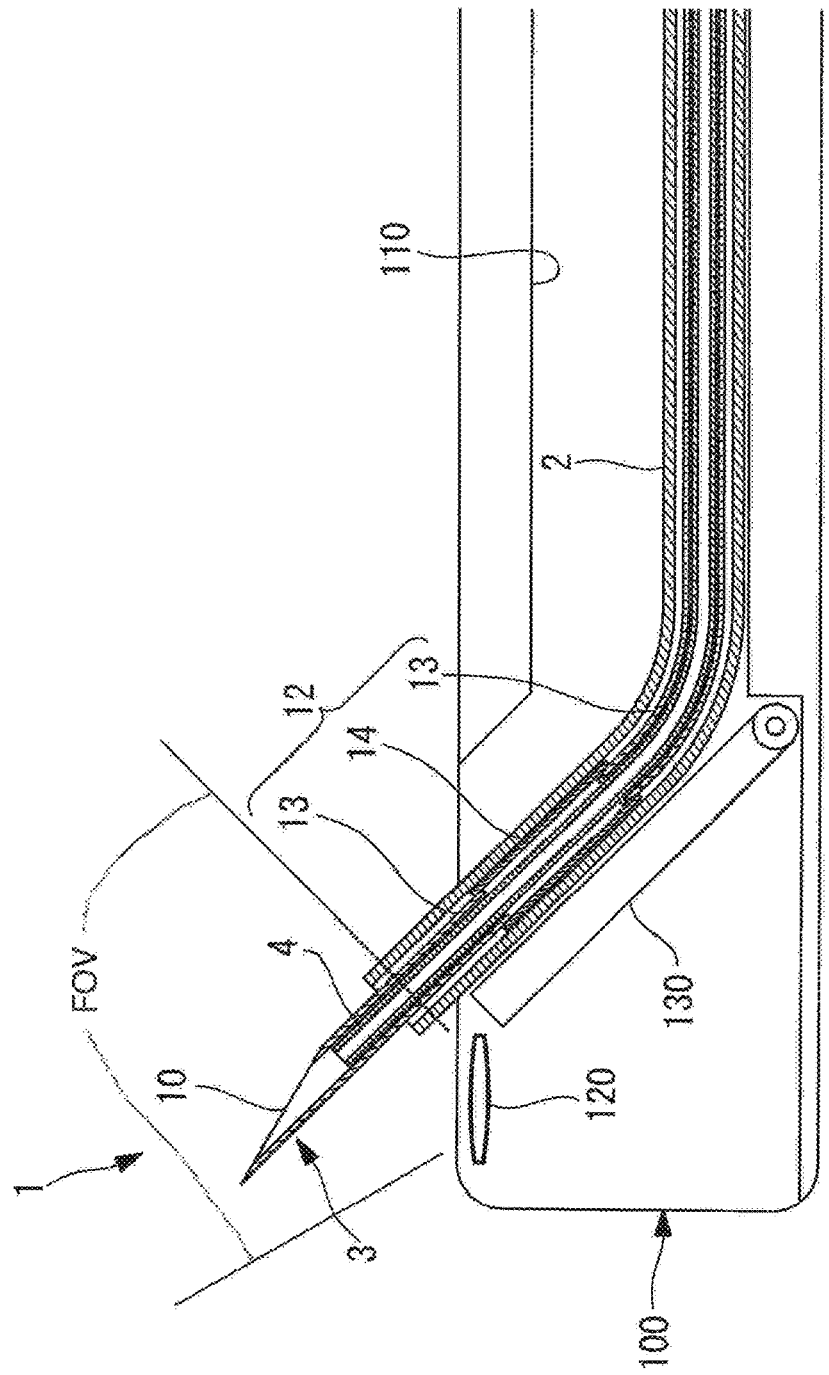
FIG. 8 is a longitudinal sectional view illustrating another example of the positional relationship between the raising platform of the endoscope that has the puncture needle in FIG. 1 inserted into the channel thereof and the joint section provided in the puncture needle.

In particular, as illustrated in FIGS. 7 and 8, in the case where the ultrasound endoscope 100 includes an observational optical system 120 and a raising platform 130 that presses and bends the tip portion of the needle tube 3 in a radial direction, in a state where the distal end of the sheath 2, which extends along the channel 110 provided in the ultrasound endoscope 100 and has been made to protrude from the distal end of the channel 110, is arranged inside the observational field of view FOV of the observational optical system 120 and the needle slider 7 has been maximally moved forward with respect to the sheath slider 6, the step portion 16 and the protrusion 17 are preferably not aligned with the raising platform 130. This is because it is difficult for the raising platform 130 to bend the parts where the step portion 16 and the protrusion 17 are provided due to the increased rigidity provided by the connection tube 14.

In other words, it is preferable that the step portion 16 and the protrusion 17 be arranged nearer the proximal end side than the proximal end of the raising platform 130 is, as illustrated in FIG. 7. Alternatively, as illustrated in FIG. 8, the step portion 16 and the protrusion 17 may be arranged nearer the distal end side than the part that is bent by the raising platform 130 is.

The needle tip 10 of the needle tube 3 and the tip portion of the protective tube 4 may be positioned on the scanning plane of ultrasound waves generated by the ultrasound sensor when the needle tube 3 has been moved forward until the protrusion 17 abuts the step portion 16 with the distal end of the sheath 2 positioned inside the observational field of view FOV of the observational optical system 120.

The puncture needle 1 may be used together with an endoscope without an ultrasound sensor instead of the ultrasound endoscope 100.

Figure 9:
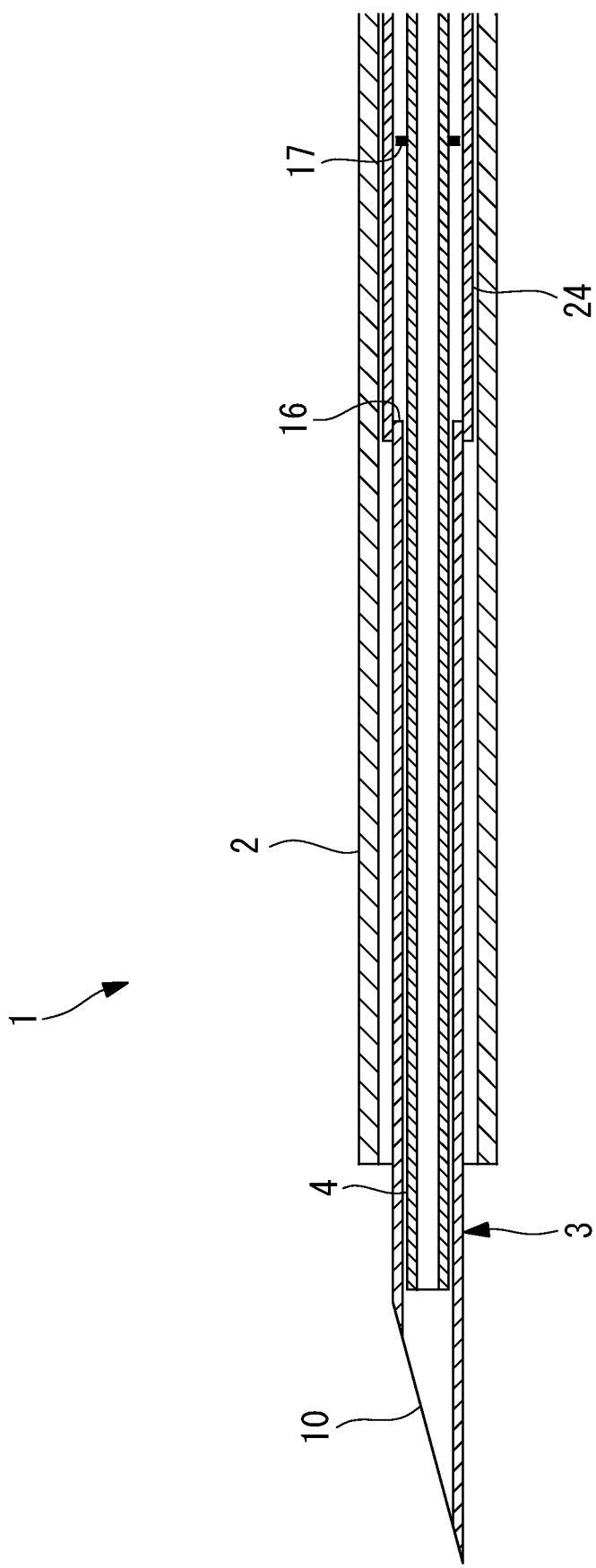
FIG. 9 is a partial longitudinal sectional view illustrating a modification of the puncture needle in FIG. 1.

In the present embodiment, the step portion 16 is formed by arranging the end faces of the two tubular parts 13 forming the needle tube 3 so as to be spaced apart in the longitudinal axis direction and then joining together the end surfaces in a state where the two tubular parts 13 have been fitted into the inside of the large-diameter connection tube 14, but alternatively, the step portion 16 may be provided only on the distal end side by joining a tubular member 24, which has a larger diameter than the needle tube 3, to the proximal end of the needle tube 3 having the needle tip 10, as illustrated in FIG. 9.

Figure 10:
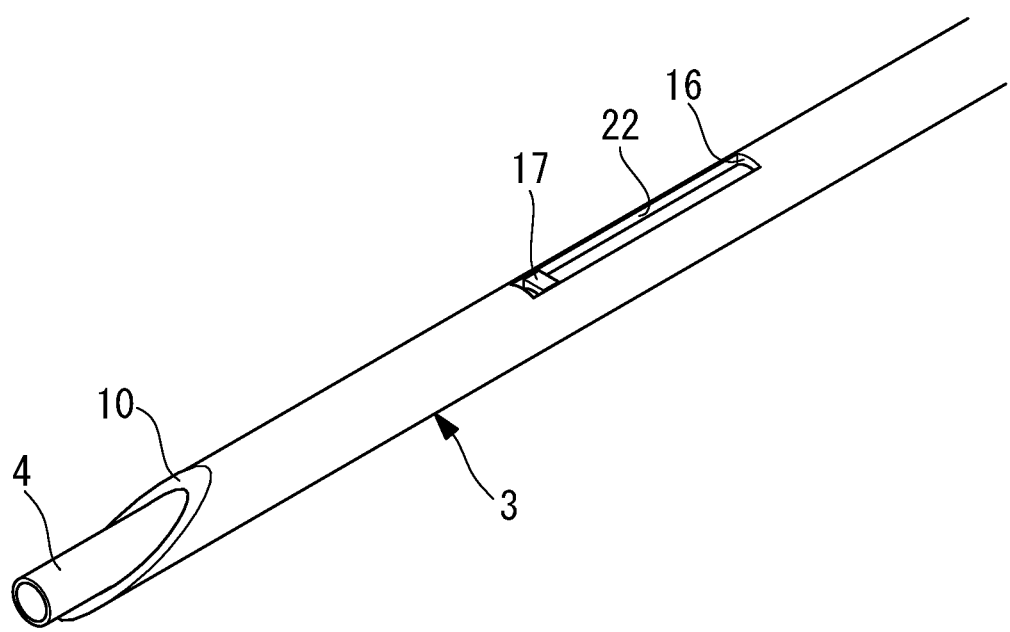
FIG. 10 is a perspective view illustrating another modification of the puncture needle in FIG. 1.

In this embodiment, the step portion 16 is formed by the connection tube 14, but alternatively, as illustrated in FIG. 10, the step portion 16 may be formed by providing a slit 22 that extends in the longitudinal axis direction at a position midway along the needle tube 3 in the longitudinal axis direction and arranging the protrusion 17 of the protective tube 4 inside the slit 22. The protective tube 4 can be maintained in a state of protruding from the needle tip 10 by making the protrusion 17 of the protective tube 4 abut the end surface of the slit 22.

Figure 11:
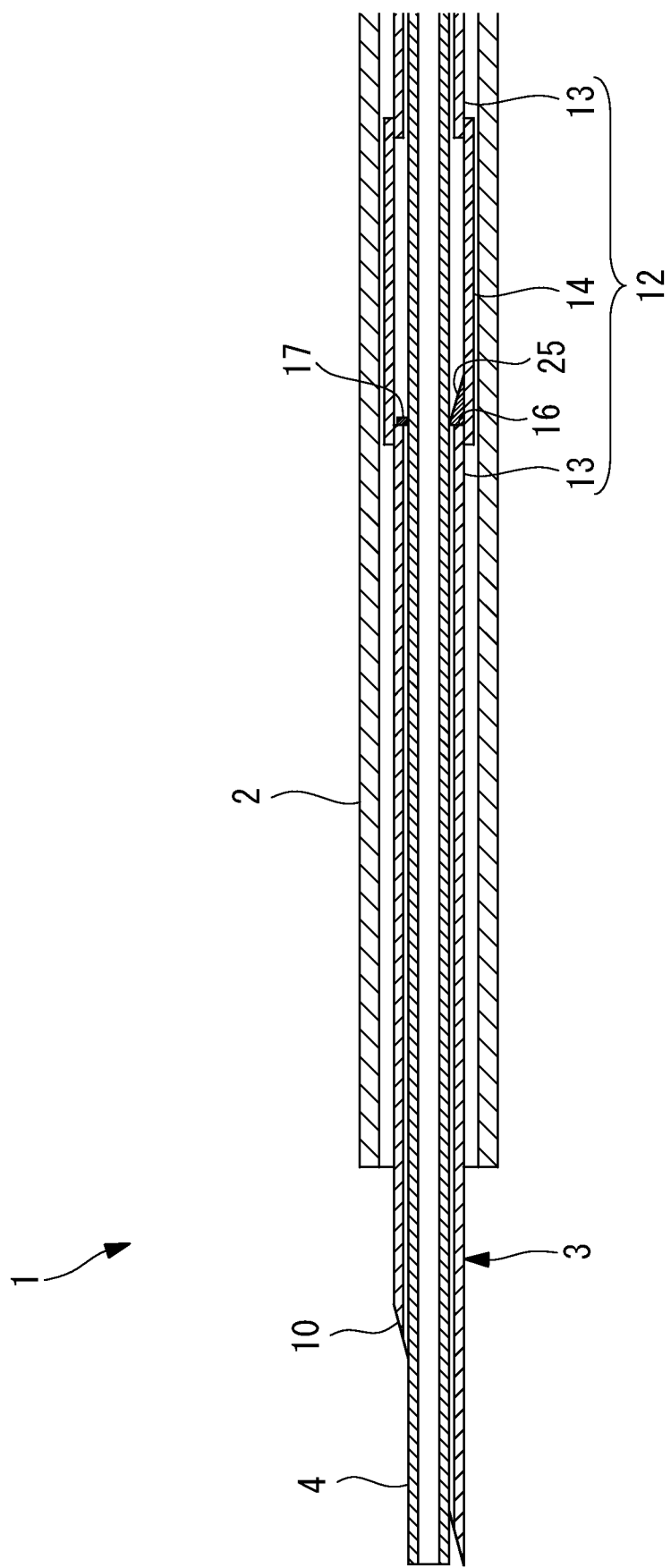
FIG. 11 is a longitudinal sectional view illustrating another modification of the puncture needle in FIG. 1.

In this embodiment, an inclined portion 25 that is inwardly radially inclined may be provided on an inner surface of the connection tube 14, as illustrated in FIG. 11. In this case, the inclined portion 25 is formed so as to be gradually inclined radially inward with increasing proximity to the step portion 16 from a position a predetermined range away from the step portion 16 on the proximal end side and so as to contact the outer surface of the protective tube 4 at the position of the step portion 16. The protrusion 17 of the protective tube 4 is preferably provided on the opposite side from the inclined portion 25 with the protective tube 4 interposed therebetween.

Figure 12:
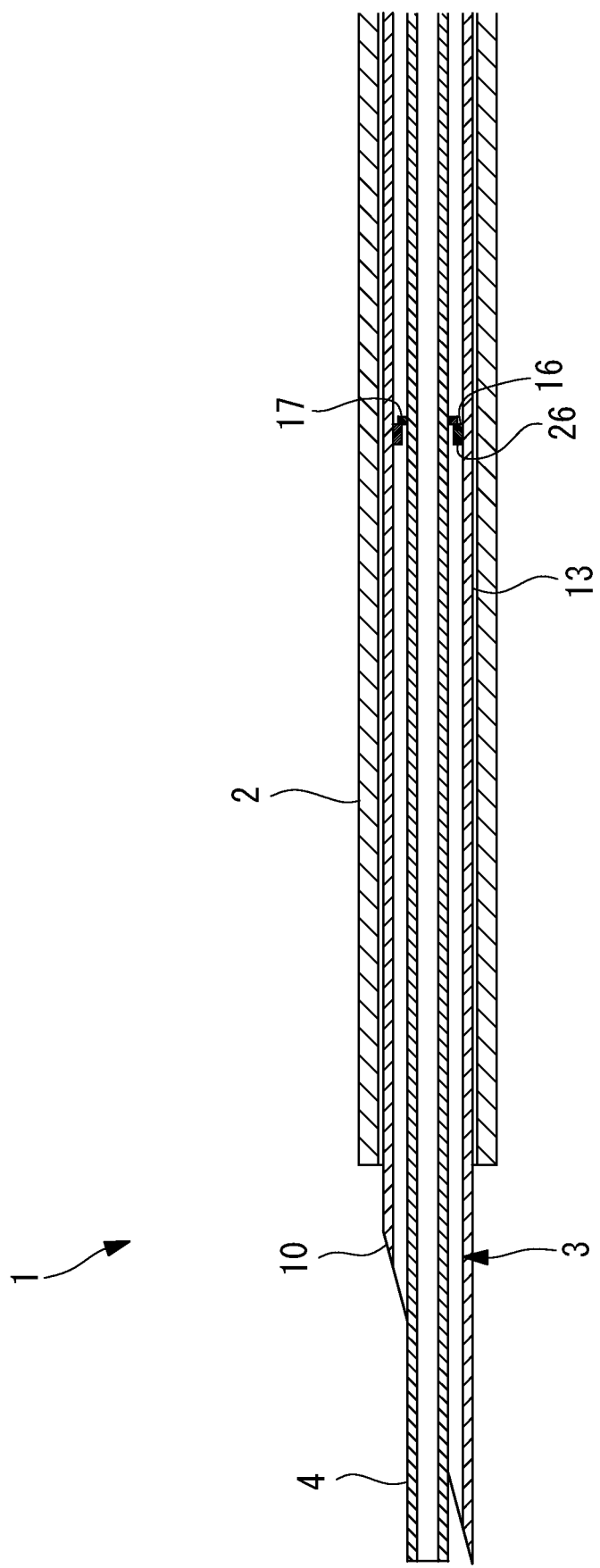
FIG. 12 is a longitudinal sectional view illustrating another modification of the puncture needle in FIG. 1.

In this embodiment, as illustrated in FIG. 12, the needle tube 3 need not include the connection tube 14 and may be formed of a single tubular part 13. In this case, a protruding portion 26, which protrudes radially inward, is provided on the inner surface of the tubular part 13 and the step portion 16 is formed by this protruding portion 26 and the inner surface of the tubular part 13. As a result, when the protective tube 4 is moved forward and made to protrude from the needle tip 10 of the needle tube 3, the protrusion 17 of the protective tube 4 abuts the step portion 16 formed by the protruding portion 26 of the tubular part 13.

As illustrated in FIG. 3, the needle slider 7 may include an engagement portion 23 that engages with the tube slider 8 when the needle slider 7 is moved forward along the longitudinal axis with respect to the sheath slider 6. As a result, puncturing can be performed using the needle tube 3 while maintaining the positional relationship between the needle tube 3 and the protective tube 4 constant.

In n this embodiment, an example of the fixing mechanism 19 that includes the recess 20 provided in the needle slider 7 and the hook 21 provided on the tube slider 8 has been illustrated, but alternatively, a mechanism may be employed that allows the two objects to be fixed to and released from each other via screw fastening.

Figure 13:
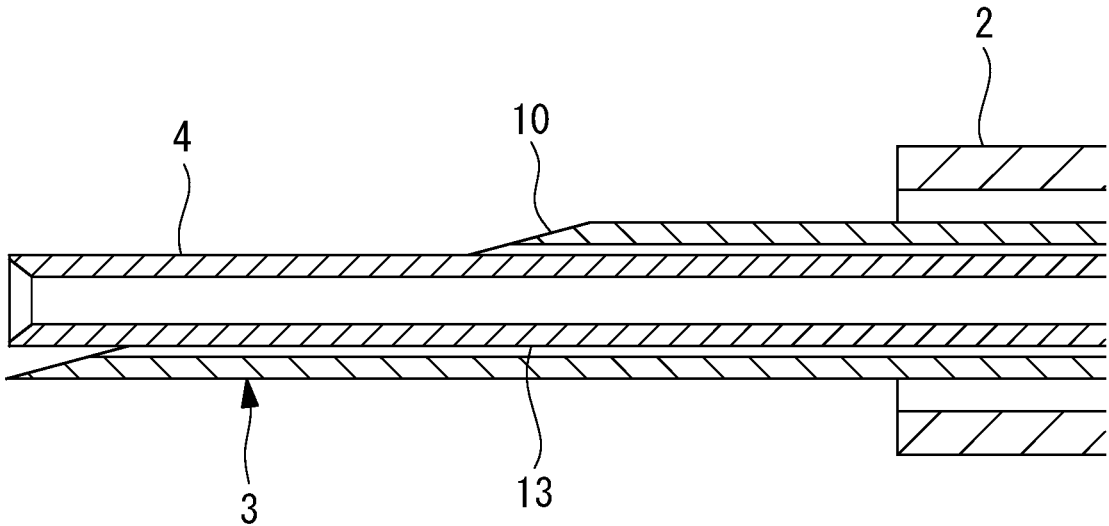
FIG. 13 is a longitudinal sectional view illustrating another modification of a puncture needle tip in FIG. 1.
Figure 14:
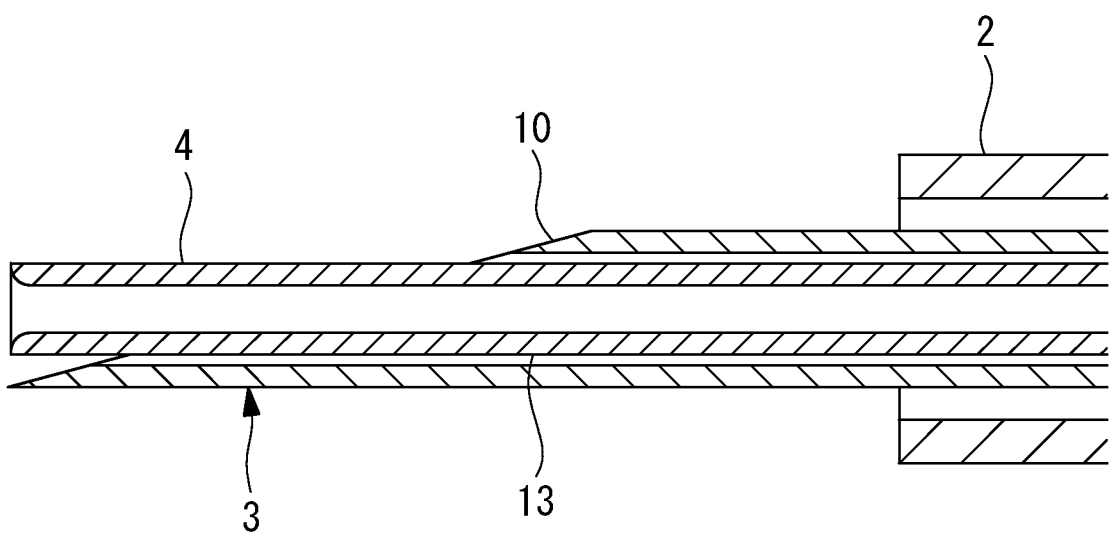
FIG. 14 is a longitudinal sectional view illustrating another modification of the puncture needle tip in FIG. 1.
Figure 15:
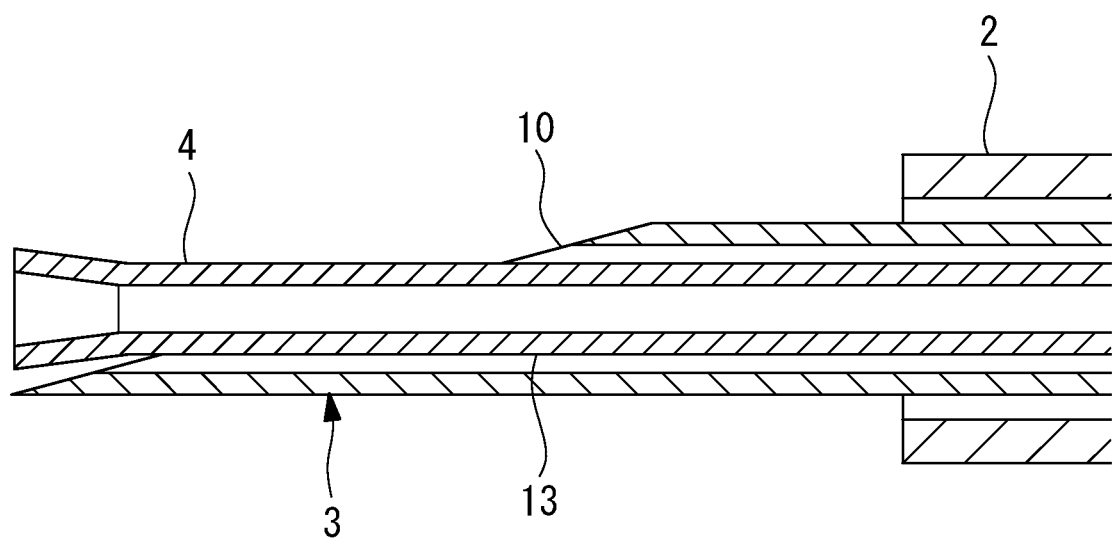
FIG. 15 is a longitudinal sectional view illustrating another modification of the puncture needle tip in FIG. 1.

In this embodiment, as illustrated in FIG. 13, a protective tube in which the inner surface of the tip is a chamfered tapered surface may be used as the protective tube 4. Thus, it is possible to suppress damage to the guide wire 15 caused by a large pressure acting on the outer surface of the guide wire 15 from the inner surface of the distal end of the protective tube 4 when the guide wire 15 is made to protrude from the protective tube 4. As illustrated in FIG. 14, the inner surface of the distal end of the protective tube 4 may be a rounded surface, or as illustrated in FIG. 15, the inner diameter of the protective tube 4 may gradually increase with increasing proximity to the distal end of the protective tube 4 from a position a predetermined distance away from the distal end of the protective tube 4 on the proximal end side.

Figure 16:
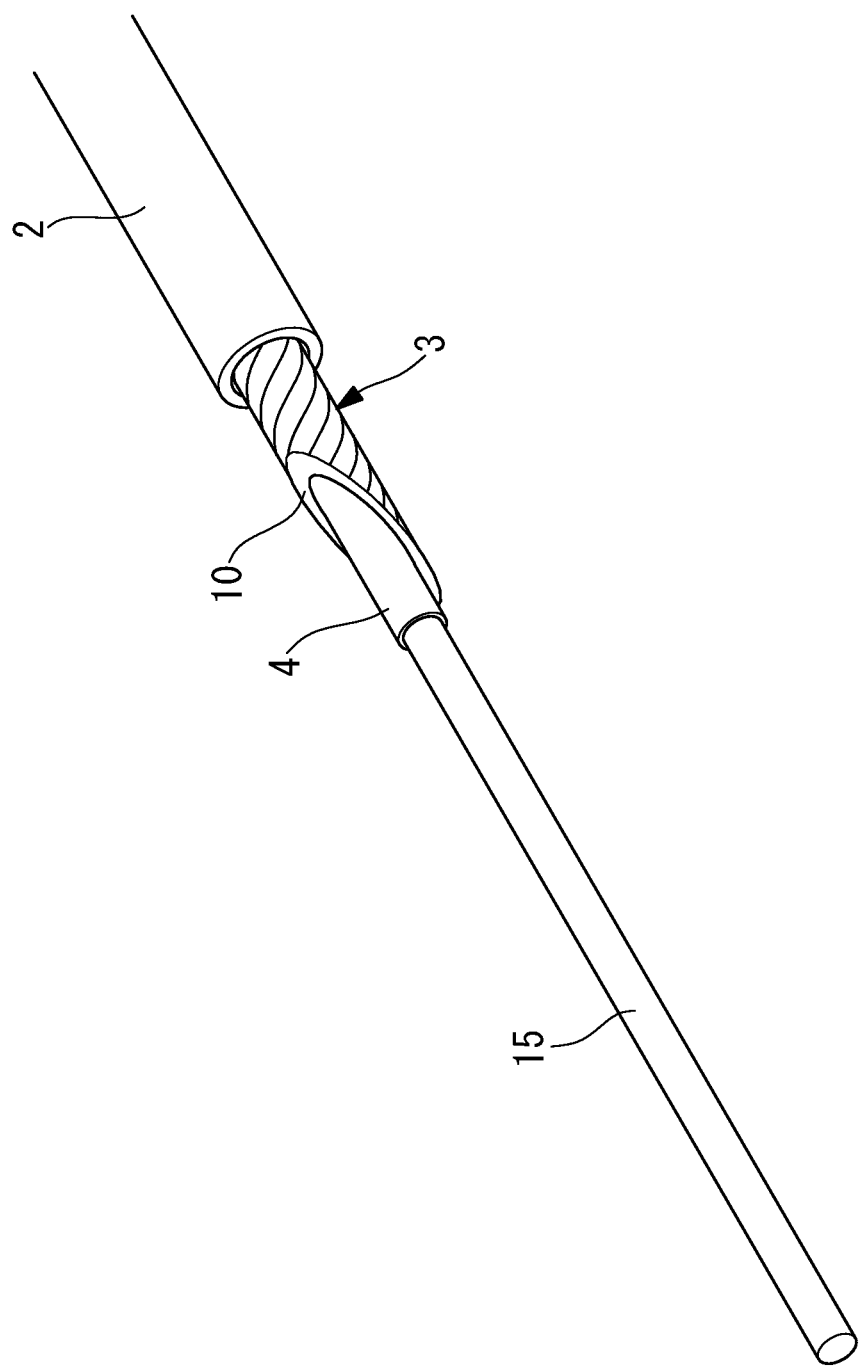
FIG. 16 is a perspective view illustrating another modification of the puncture needle tip in FIG. 1.

In this embodiment, as illustrated in FIG. 16, a spiral cut (for example, a laser cut) may be formed in the outer peripheral surface of the tubular part 13 that is located nearer the distal end side than the connection tube 14 of the needle tube 3. In this case, the tubular part 13 that is located nearer the proximal end side than the connection tube 14 of the needle tube 3 is formed of stainless steel. This enables the tubular part 13 that is nearer the distal end side than the connection tube 14 to readily follow the curved shape of the endoscope while maintaining pushability in the tubular part 13 that is nearer the proximal end side than the connection tube 14.

As a result, the following aspect is read from the above described embodiment of the present invention.

An aspect of the present invention provides a puncture needle that includes: a tubular sheath having a longitudinal axis; a needle tube that is arranged inside the sheath so as to be movable along the longitudinal axis and that has a needle tip at a distal end thereof; a protective tube that is arranged inside the needle tube so as to be movable along the longitudinal axis and that has a lumen into which a guide wire is inserted so as to be movable along a direction of the longitudinal axis; a needle slider that is connected to a proximal end of the needle tube; and a tube slider that is supported so as to be able to move in directions along the longitudinal axis relative to the needle slider and that is connected to the proximal end of the protective tube. The needle tube has a step portion formed at a position midway along the needle tube in the longitudinal direction. The protective tube has a protrusion, which protrudes radially outward, on at least part of an outer peripheral surface thereof at a position which is nearer a proximal end side of the protective tube than the step portion is. A distal end of the protective tube is positioned at a position so as to protrude from the distal end of the needle tube when the protrusion abuts the step portion from the proximal end side of the protective tube. The needle slider is provided with a locking portion that abuts the tube slider when the tube slider is moved forward toward the distal end side relative to the needle slider, and the protrusion is maintained in a state of pressing against the step portion when the tube slider is moved forward to a position where the tube slider abuts the locking portion.

According to this aspect, when the protective tube, which is housed inside the needle tube, is moved forward relative to the needle tube after the tissue has been pierced by the needle tube, further forward movement of the protective tube relative to the needle tube is restricted by the protrusion provided on at least part of the outer peripheral surface of the protective tube abutting the step portion provided in the needle tube. At this time, the distal end of the protective tube is positioned so as to protrude from the distal end of the needle tube, and therefore it is possible to prevent the protective tube from excessively protruding from the distal end of the needle tube and to more reliably prevent the guide wire that passes through the inside of the lumen of the protective tube from contacting the needle tip of the needle tube.

With this configuration, when an operator moves the tube slider forward relative to the needle slider in order to cause the protective tube to protrude from the needle tip of the needle tube, the operator is able to recognize that the protective tube has moved forward to a position where the protrusion amount is restricted by the protrusion pressing against the step portion as a result of the tube slider having been moved forward to a position where the tube slider abuts the locking portion.

In the above-described aspect, the needle tube may include a needle tip portion that includes the needle tip of the needle tube, a needle base portion that includes a proximal end of the needle tube, and a connection tube that allows the needle tip portion to be fitted inside thereof on a distal end side thereof and allows the needle base portion to be fitted inside thereof on a proximal end side thereof, and the step portion may be formed by the connection tube and a proximal end surface of the needle tip portion fitted into the connection tube such that an inner diameter decreases by one step in the step portion toward the distal end of the needle tube.

With this configuration, when the protective tube is moved forward relative to the needle tube, the protrusion on the protective tube moves inside the connection tube along the longitudinal axis toward the distal end side and further forward movement of the protective tube relative to the needle tube is restricted by the protrusion abutting the proximal end surface of the needle tip portion of the step portion.

In the above-described aspect, a protrusion amount of the protective tube from the needle tip in a state where the tube slider has been moved forward to the position where the tube slider abuts the locking portion may be smaller than a maximum stroke amount of the tube slider.

With this configuration, the protective tube can be made to protrude from the distal end of the needle tube by an appropriate amount of protrusion at the position where the tube slider has been maximally moved forward and the protective tube can be more securely retracted toward the proximal end side from the distal end of the needle tube at the position where the tube slider has been maximally moved backward.

In the above-described aspect, the puncture needle may further include a fixing mechanism that fixes the tube slider to the needle slider in a state where the tube slider has abutted the locking portion.

With this configuration, when the tube slider is fixed to the needle slider by the fixing mechanism, the protrusion presses against the step portion and a state where the protective tube protrudes from the distal end of the needle tube by the appropriate protrusion amount can be maintained.

In the above-described aspect, the puncture needle may further include: an operation part body; and a sheath slider that is supported so as to be movable along the longitudinal axis relative to the operation part body and that is connected to a proximal end of the sheath. The needle slider may be supported so as to be movable in directions along the longitudinal axis with respect to the sheath slider.

With this configuration, the sheath can be moved forward by moving the sheath slider forward with respect to the operation part body in the longitudinal axis direction and the needle tube can be made to protrude from the distal end of the sheath by moving the needle slider forward with respect to the sheath slider in the longitudinal axis direction.

In the above-described aspect, the needle slider may include an engagement portion that engages with the tube slider when the needle slider is moved forward relative to the sheath slider.

With this configuration, when the needle slider is moved forward relative to the sheath slider, the needle tube is moved forward relative to the sheath. At this time, since the engagement portion provided on the needle slider engages with the tube slider, the protective tube is also moved forward together with the forward movement of the needle tube. As a result, the distal end of the protective tube can be held at a position close to the needle tip of the needle tube and the distal end of the protective tube can be quickly made to protrude from the needle tip after puncturing is performed using the needle tube.

In the above-described aspect, the tip portion of the protective tube may be coated with a metal powder.

This configuration enables the protrusion state of the protective tube from the distal end of the needle tube to be readily visible under X-ray or ultrasound endoscopy.

In the above-described aspect, the puncture needle may be inserted into a channel of an endoscope that includes an observational optical system, the channel, and a raising platform that is arranged at a distal end of the channel, and in a state where a distal end of the sheath, which extends along the channel and has been made to protrude from the distal end of the channel, is arranged inside an observational field of view of the observational optical system and the needle slider has been moved maximally forward with respect to the sheath slider, the step portion may be located nearer the proximal end side than a proximal end of the raising platform is.

With this configuration, the puncture needle is inserted into the channel of the endoscope, the distal end of the sheath is arranged inside the observational field of view of the observational optical system by moving the sheath slider forward, and the needle tip of the needle tube can be made to protrude from the distal end of the sheath by maximally moving the needle slider forward with respect to the sheath slider. In this state, the direction of the needle tip of the needle tube is adjusted by raising the sheath and the needle tube by activating the raising platform.

In the vicinity of the step portion provided in the needle tube, the diameter of the needle tube is larger at the proximal end side than at the step portion and therefore this is a region where it is difficult for the puncture needle to bend when the puncture needle is raised. According to this aspect, even when the needle tube is maximally moved forward, the puncture needle can be smoothly bent by the operation of the raising platform by arranging the step portion that is difficult to bend further toward the proximal end side than the proximal end of the raising platform.

In the above-described aspect, the puncture needle may be used together with an endoscope that includes an observational optical system, a channel, and an ultrasound sensor, and when a distal end of the sheath, which extends along the channel and is made to protrude from the distal end of the channel, is arranged inside an observational field of view of the observational optical system and the protrusion abuts the step portion, the needle tube and a tip portion of the protective tube may be located inside a detection range of the ultrasound sensor.

In the above-described aspect, a stroke range of the needle tube may be defined as being between a first position at which the needle tube protrudes from a distal end of the sheath and a second position at which the needle tube is retracted toward a proximal end side from the distal end of the sheath.

Another aspect of the present invention provides a method of using a guide wire, including: forming a through hole by puncturing a needle tube from the inside of a first lumen through a wall of the first lumen and a wall of a second lumen and arranging a needle tip of the needle tube inside the second lumen; moving a protective tube housed inside the needle tube forward along a longitudinal axis until a protrusion provided on at least part of an outer peripheral surface of the protective tube abuts a step portion provided inside the needle tube and thereby make a tip portion of the protective tube protrude from the needle tip of the needle tube; maintaining the protrusion in a state of pressing against the step portion from the proximal end side by moving forward the tube slider connected to the proximal end of the protective tube relative to the needle slider connected to the proximal end of the needle tube in a state where the protrusion has abutted the step portion; making a guide wire, which extends through the inside of the protective tube, protrude from a distal end of the protective tube into the inside of the second lumen; and positioning the guide wire from the first lumen to the second lumen by removing the needle tube and the protective tube from the through hole.

In the above-described aspect, the method may further include: inserting a tip portion of a stent deploying device into the second lumen along the positioned guide wire; dilating a tip portion of a stent deployed from the stent deploying device in the second lumen and dilating a proximal end portion of the stent in the first lumen; and connecting the wall of the first lumen and the wall of the second lumen.

REFERENCE SIGNS LIST 1 puncture needle
2 sheath
3 needle tube
4 protective tube
5 operation part body
6 slider sheath
7 needle slider
8 tube slider
10 needle tip
13 tubular parts (needle tip portion, needle base portion)
14 connection tube
15 guide wire
16 step portion
17 protrusion
18 locking portion
19 fixing mechanism
23 engagement portion
100 ultrasound endoscope (endoscope)
110 channel
120 observational optical system
130 raising platform

The invention claimed is:

1. A puncture needle comprising:
a tubular sheath having a longitudinal axis;
a needle tube that is arranged inside the sheath so as to be movable along the longitudinal axis and that has a needle tip at a distal end thereof;
a protective tube that is arranged inside the needle tube so as to be movable along the longitudinal axis and that has a lumen into which a guide wire is inserted so as to be movable along a direction of the longitudinal axis;
a needle slider that is connected to a proximal end of the needle tube; and
a tube slider that is supported so as to be able to move in directions along the longitudinal axis relative to the needle slider and that is connected to the proximal end of the protective tube;
wherein the needle tube has a step portion formed at a position midway along the needle tube in the longitudinal direction,
the protective tube has a protrusion, which protrudes radially outward, on at least part of an outer peripheral surface thereof at a position which is nearer a proximal end side of the protective tube than the step portion is, and
a distal end of the protective tube is positioned at a position so as to protrude from the distal end of the needle tube when the protrusion abuts the step portion from the proximal end side of the protective tube,
the needle slider is provided with a locking portion that abuts the tube slider when the tube slider is moved forward toward the distal end side relative to the needle slider, and
the protrusion is maintained in a state of pressing against the step portion when the tube slider is moved forward to a position where the tube slider abuts the locking portion.

2. The puncture needle according to claim 1,
wherein the needle tube includes a needle tip portion that includes the needle tip of the needle tube, a needle base portion that includes a proximal end of the needle tube, and a connection tube that allows the needle tip portion to be fitted inside thereof on a distal end side thereof and allows the needle base portion to be fitted inside thereof on a proximal end side thereof, and
the step portion is formed by the connection tube and a proximal end surface of the needle tip portion fitted into the connection tube such that an inner diameter decreases by one step in the step portion toward the distal end of the needle tube.

3. The puncture needle according to claim 1,
wherein a protrusion amount of the protective tube from the needle tip in a state where the tube slider has been moved forward to the position where the tube slider abuts the locking portion is smaller than a maximum stroke amount of the tube slider.

4. The puncture needle according to claim 1, further comprising:
a fixing mechanism that fixes the tube slider to the needle slider in a state where the tube slider has abutted the locking portion.

5. The puncture needle according to claim 1, further comprising:
an operation part body; and
a sheath slider that is supported so as to be movable along the longitudinal axis relative to the operation part body and that is connected to a proximal end of the sheath,
wherein the needle slider is supported so as to be movable in directions along the longitudinal axis with respect to the sheath slider.

6. The puncture needle according to claim 5,
wherein the needle slider includes an engagement portion that engages with the tube slider when the needle slider is moved forward relative to the sheath slider.

7. The puncture needle according to claim 1,
wherein the tip portion of the protective tube is coated with a metal powder.

8. The puncture needle according to claim 5,
wherein the puncture needle is inserted into a channel of an endoscope that includes an observational optical system, the channel, and a raising platform that is arranged at a distal end of the channel, and
in a state where a distal end of the sheath, which extends along the channel and has been made to protrude from the distal end of the channel, is arranged inside an observational field of view of the observational optical system and the needle slider has been moved maximally forward with respect to the sheath slider, the step portion is located nearer the proximal end side than a proximal end of the raising platform is.

9. The puncture needle according to claim 1,
wherein the puncture needle is used together with an endoscope that includes an observational optical system, a channel, and an ultrasound sensor, and
when a distal end of the sheath, which extends along the channel and is made to protrude from the distal end of the channel, is arranged inside an observational field of view of the observational optical system and the protrusion abuts the step portion, the needle tube and a tip portion of the protective tube are located inside a detection range of the ultrasound sensor.

10. The puncture needle according to claim 1,
wherein a stroke range of the needle tube is defined as being between a first position at which the needle tube protrudes from a distal end of the sheath and a second position at which the needle tube is retracted toward a proximal end side from the distal end of the sheath.

11. A method of using a guide wire, comprising:
forming a through hole by puncturing a needle tube from the inside of a first lumen through a wall of the first lumen and a wall of a second lumen and arranging a needle tip of the needle tube inside the second lumen;
moving a protective tube housed inside the needle tube forward along a longitudinal axis until a protrusion provided on at least part of an outer peripheral surface of the protective tube abuts a step portion provided inside the needle tube and thereby make a tip portion of the protective tube protrude from the needle tip of the needle tube;
maintaining the protrusion in a state of pressing against the step portion from the proximal end side by moving forward the tube slider connected to the proximal end of the protective tube relative to the needle slider connected to the proximal end of the needle tube in a state where the protrusion has abutted the step portion,
making a guide wire, which extends through the inside of the protective tube, protrude from a distal end of the protective tube into the inside of the second lumen; and
positioning the guide wire from the first lumen to the second lumen by removing the needle tube and the protective tube from the through hole.

12. The method of using a guide wire according to claim 11, further comprising:
inserting a tip portion of a stent deploying device into the second lumen along the positioned guide wire;
dilating a tip portion of a stent deployed from the stent deploying device in the second lumen and dilating a proximal end portion of the stent in the first lumen; and
connecting the wall of the first lumen and the wall of the second lumen.

13. A puncture needle comprising:
a tubular sheath having a longitudinal axis;
a needle tube that is arranged inside the sheath so as to be movable along the longitudinal axis and that has a needle tip at a distal end thereof; and
a protective tube that is arranged inside the needle tube so as to be movable along the longitudinal axis and that has a lumen into which a guide wire is inserted so as to be movable along a direction of the longitudinal axis;
wherein the needle tube includes a needle tip portion that includes the needle tip of the needle tube, a needle base portion that includes a proximal end of the needle tube, and a connection tube that allows the needle tip portion to be fitted inside thereof on a distal end side thereof and allows the needle base portion to be fitted inside thereof on a proximal end side thereof, and a step portion formed by the connection tube and a proximal end surface of the needle tip portion fitted into the connection tube such that an inner diameter decreases by one step in the step portion toward the distal end of the needle tube, and
wherein the protective tube has a protrusion, which protrudes radially outward, on at least part of an outer peripheral surface thereof at a position which is nearer a proximal end side of the protective tube than the step portion is, and
a distal end of the protective tube is positioned at a position so as to protrude from the distal end of the needle tube when the protrusion abuts the step portion from the proximal end side of the protective tube.

14. The puncture needle according to claim 13, further comprising:
a needle slider that is connected to a proximal end of the needle base portion; and
a tube slider that is supported so as to be able to move in directions along the longitudinal axis relative to the needle slider and that is connected to the proximal end of the protective tube;
wherein the needle slider is provided with a locking portion that abuts the tube slider when the tube slider is moved forward toward the distal end side relative to the needle slider, and
the protrusion is maintained in a state of pressing against the step portion when the tube slider is moved forward to a position where the tube slider abuts the locking portion.

15. The puncture needle according to claim 14,
wherein a protrusion amount of the protective tube from the needle tip in a state where the tube slider has been moved forward to the position where the tube slider abuts the locking portion is smaller than a maximum stroke amount of the tube slider.

16. The puncture needle according to claim 14, further comprising:
a fixing mechanism that fixes the tube slider to the needle slider in a state where the tube slider has abutted the locking portion.

17. The puncture needle according to claim 14, further comprising:
an operation part body; and
a sheath slider that is supported so as to be movable along the longitudinal axis relative to the operation part body and that is connected to a proximal end of the sheath,
wherein the needle slider is supported so as to be movable in directions along the longitudinal axis with respect to the sheath slider.

18. The puncture needle according to claim 17,
wherein the needle slider includes an engagement portion that engages with the tube slider when the needle slider is moved forward relative to the sheath slider.
19. The puncture needle according to claim 13,
wherein the tip portion of the protective tube is coated with a metal powder.
20. The puncture needle according to claim 13,
wherein a stroke range of the needle tube is defined as being between a first position at which the needle tube protrudes from a distal end of the sheath and a second position at which the needle tube is retracted toward a proximal end side from the distal end of the sheath.

\* \* \* \* \*